US011771783B2

(12) United States Patent
Lee et al.

(10) Patent No.: US 11,771,783 B2
(45) Date of Patent: Oct. 3, 2023

(54) STERILIZER FOR VEHICLE AND CONTROL METHOD THEREOF

(71) Applicants: HYUNDAI MOTOR COMPANY, Seoul (KR); KIA MOTORS CORPORATION, Seoul (KR); KAIS Inc., Pyeongtaek-si (KR)

(72) Inventors: Jae Seung Lee, Hwaseong-si (KR); Young Hoon Ji, Osan-si (KR)

(73) Assignees: HYUNDAI MOTOR COMPANY, Seoul (KR); KIA MOTORS CORPORATION, Seoul (KR)

( * ) Notice: Subject to any disclaimer, the term of this patent is extended or adjusted under 35 U.S.C. 154(b) by 251 days.

(21) Appl. No.: 17/154,001

(22) Filed: Jan. 21, 2021

(65) Prior Publication Data

US 2022/0062466 A1   Mar. 3, 2022

(30) Foreign Application Priority Data

Sep. 3, 2020   (KR) .......................... 10-2020-0112253

(51) Int. Cl.
*A61L 2/10*   (2006.01)
*A61L 2/24*   (2006.01)
*B60R 15/00*   (2006.01)

(52) U.S. Cl.
CPC .................. *A61L 2/10* (2013.01); *A61L 2/24* (2013.01); *B60R 15/00* (2013.01); *A61L 2202/11* (2013.01); *A61L 2202/14* (2013.01); *A61L 2202/25* (2013.01)

(58) Field of Classification Search
CPC ..... A61L 2/10; A61L 2/24; A61L 2/26; A61L 2202/11; A61L 2202/14; A61L 2202/25; A61L 2202/123; B60R 15/00; B60Q 3/59
See application file for complete search history.

(56) References Cited

U.S. PATENT DOCUMENTS

| 2010/0104471 | A1* | 4/2010 | Harmon .................. A61L 2/10 422/186.3 |
| 2017/0304473 | A1* | 10/2017 | Farren .................. H01J 37/244 |
| 2018/0064833 | A1* | 3/2018 | Childress ................ A61L 2/10 |
| 2021/0187140 | A1* | 6/2021 | Spazier .................. B60S 1/64 |
| 2022/0024288 | A1* | 1/2022 | Geum .................... B60Q 3/53 |
| 2022/0088250 | A1* | 3/2022 | Baarman .................. A61L 2/24 |

FOREIGN PATENT DOCUMENTS

| BG | 495499 A * 11/1938 .............. A61L 2/10 |
| KR | 10-2015-0017544 A   2/2015 |

* cited by examiner

*Primary Examiner* — Jennifer Wecker
*Assistant Examiner* — Brady C Pilsbury
(74) *Attorney, Agent, or Firm* — Morgan, Lewis & Bockius LLP

(57) ABSTRACT

A sterilizer for a vehicle includes: a module bracket fixed to an interior component of a vehicle; a slider slidably mounted on the module bracket; a module case connected to the slider; a sterilization module disposed within the module case and configured to radiate ultraviolet rays to an outside; and a motor fixed to the module bracket to drive the slider by a passenger's request.

15 Claims, 8 Drawing Sheets

[FIG. 1]
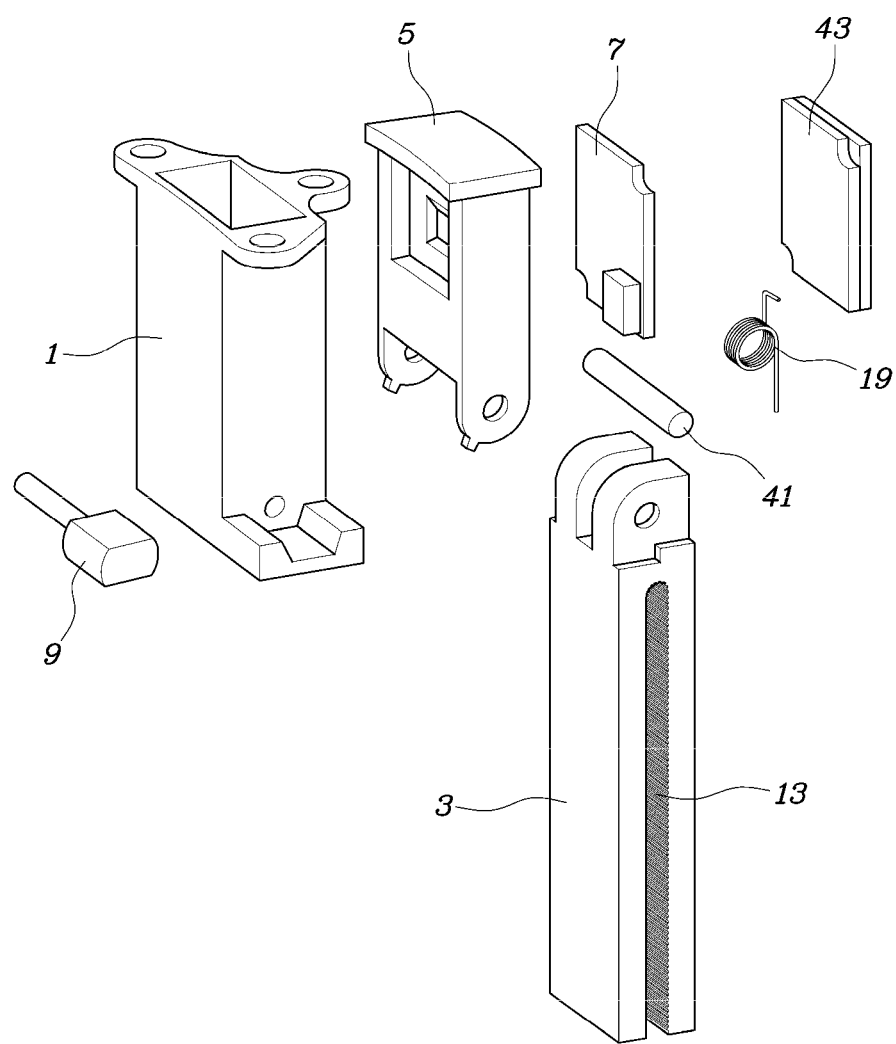

[FIG. 2]
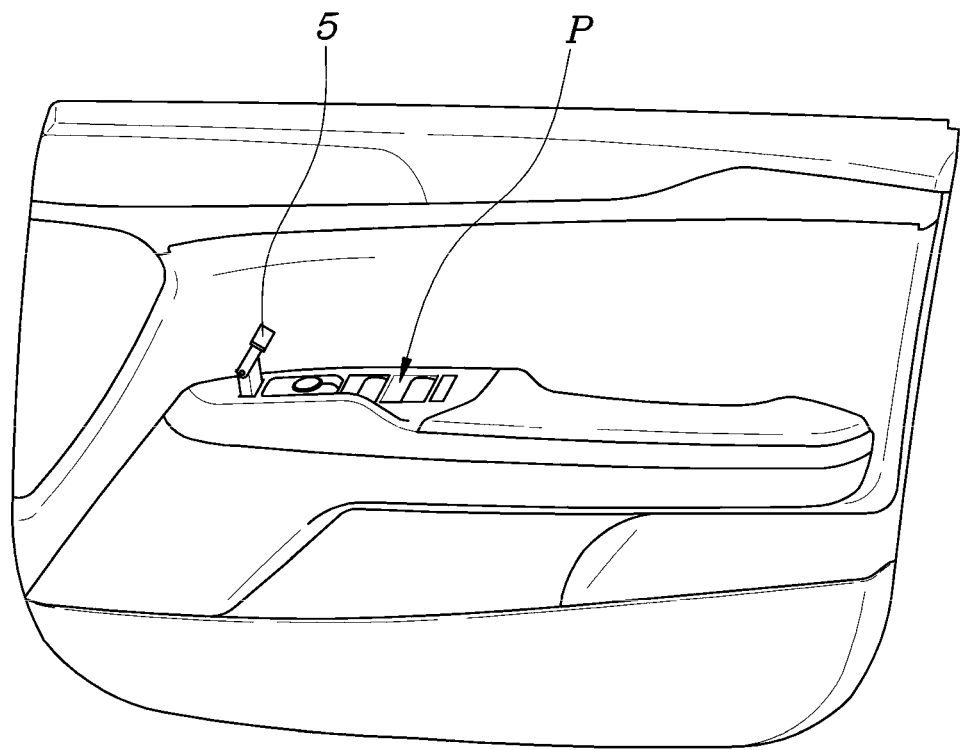

[FIG. 3]
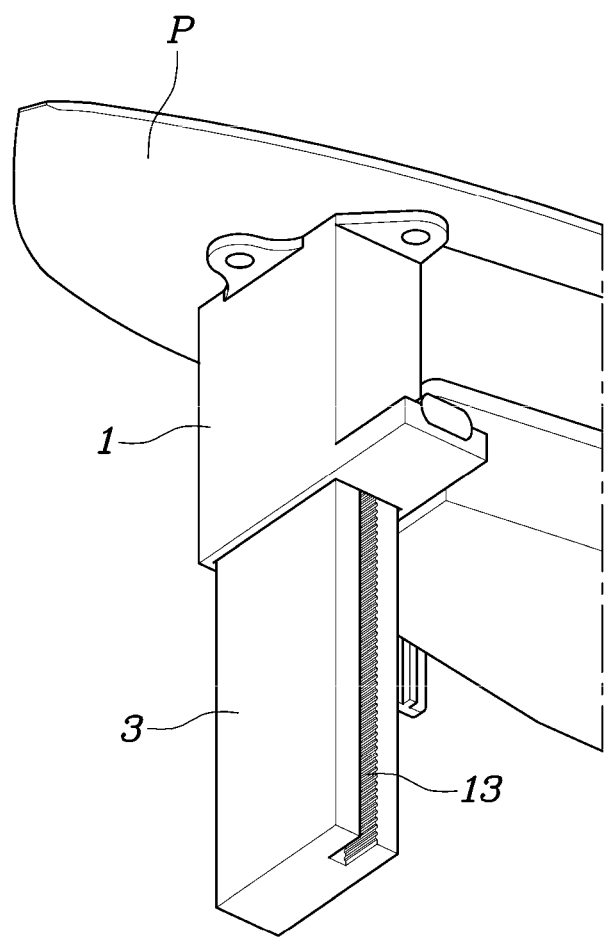

[FIG. 4]
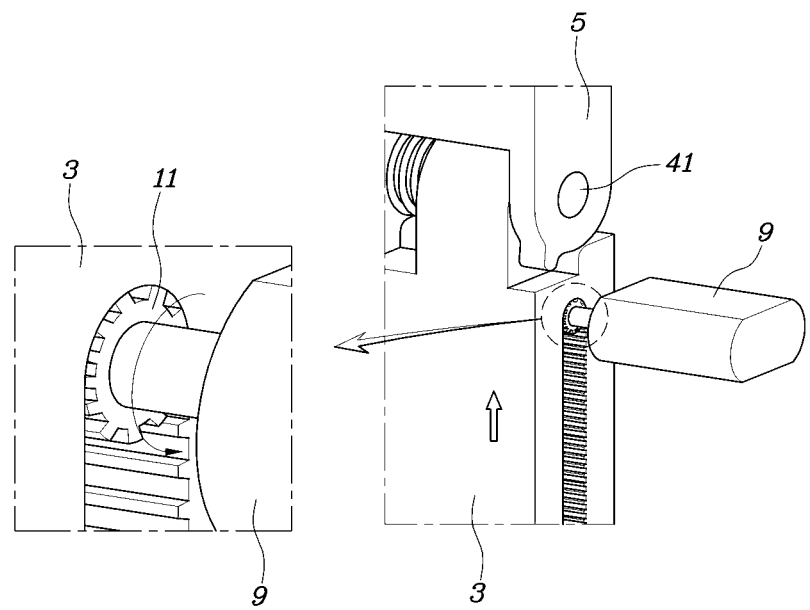
[FIG. 5]
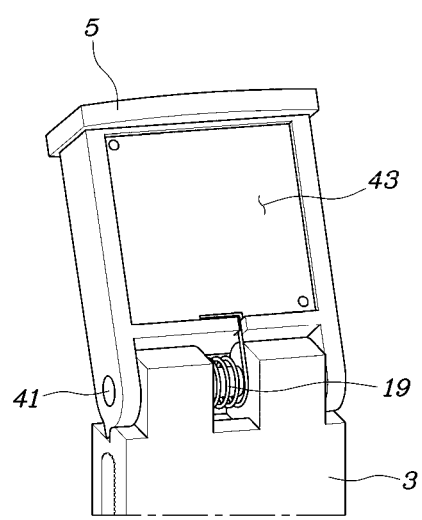

[FIG. 6]
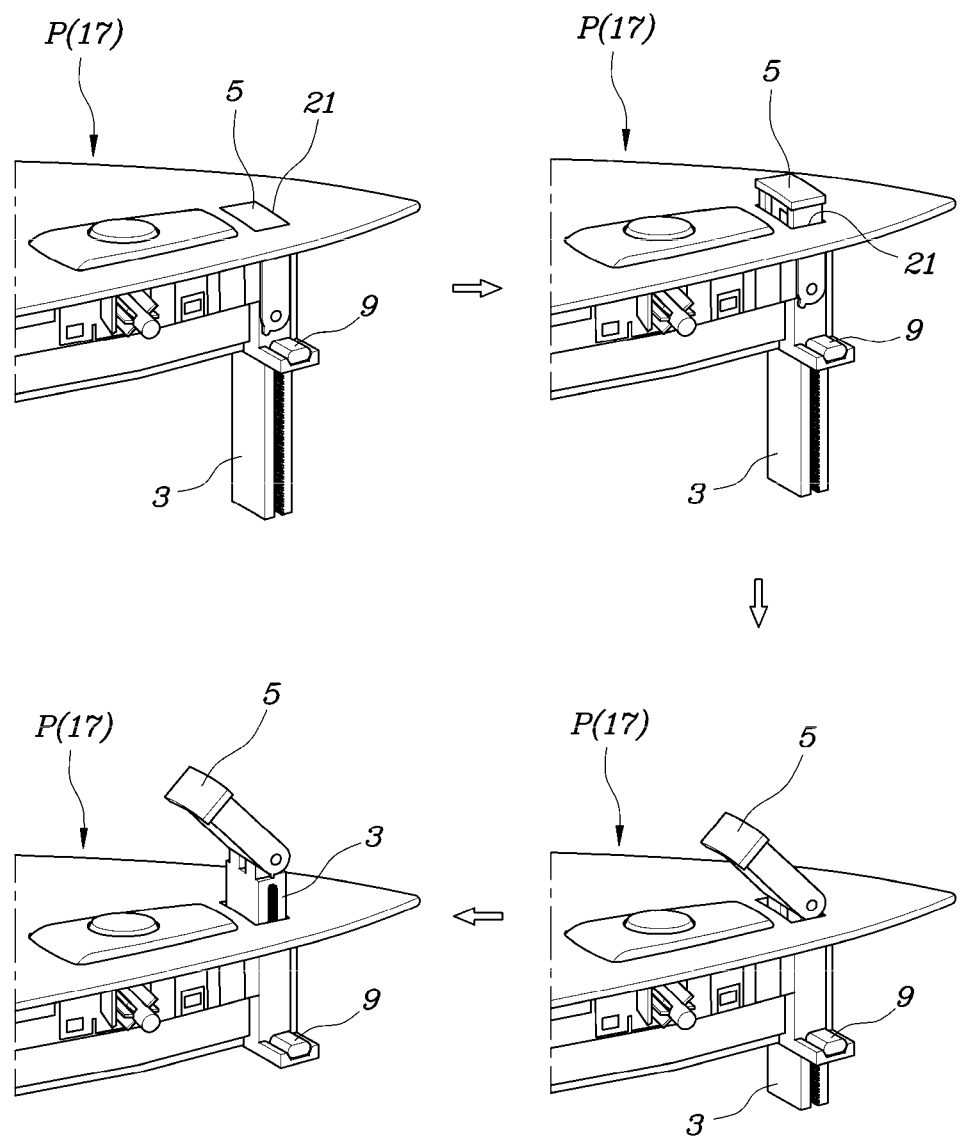

[FIG. 7]
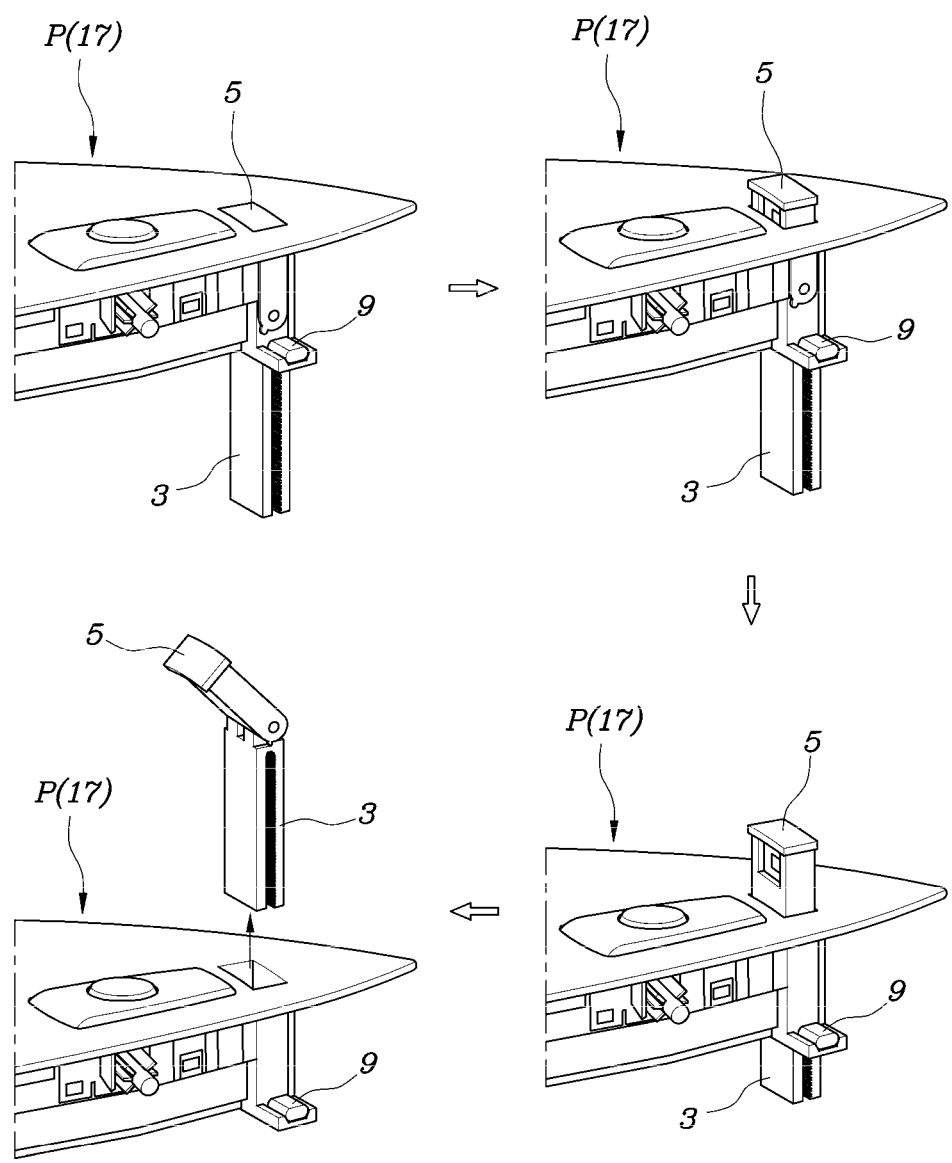

[FIG. 8]
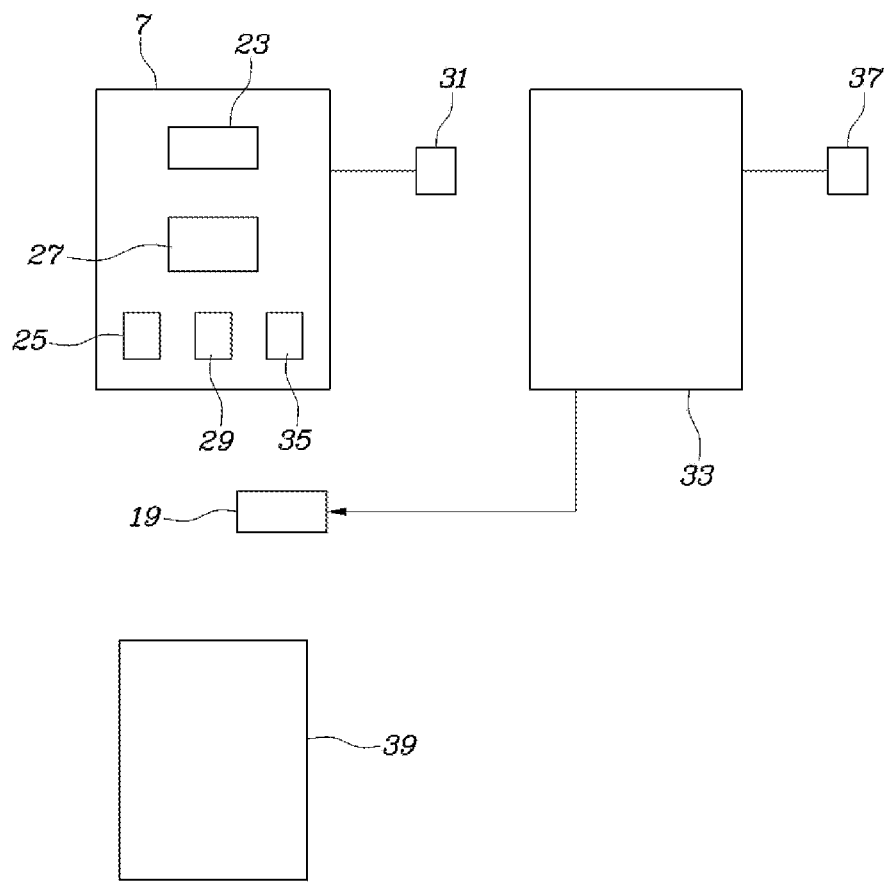

[FIG. 9]
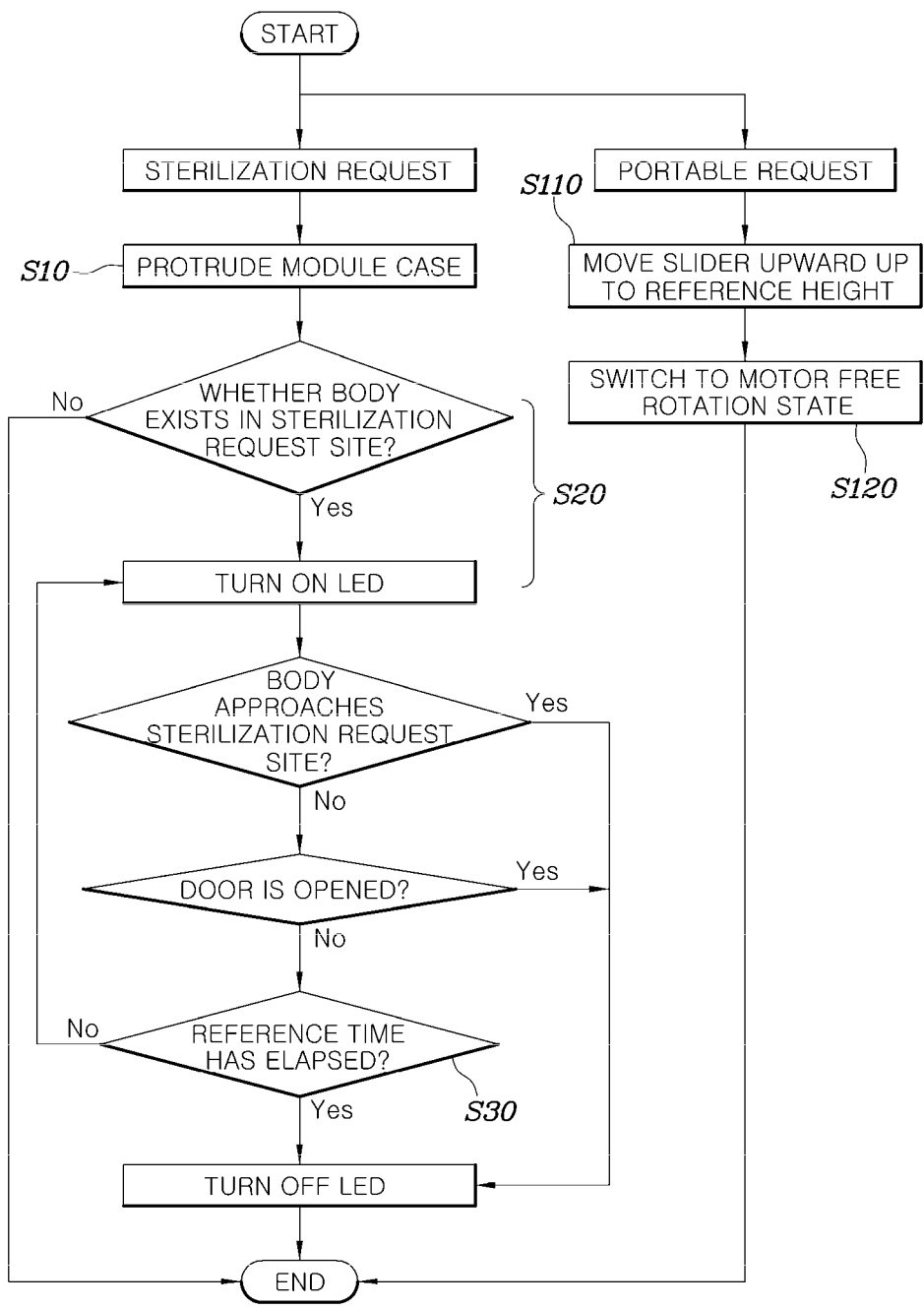

STERILIZER FOR VEHICLE AND CONTROL METHOD THEREOF

CROSS REFERENCE TO RELATED APPLICATION

The present application claims the benefit of priority to Korean Patent Application No. 10-2020-0112253, filed on Sep. 3, 2020 in the Korean Intellectual Property Office, the entire contents of which is incorporated herein by reference.

TECHNICAL FIELD

The present disclosure relates to a sterilizer for a vehicle, and more specifically, is a technology about an apparatus for locally sterilizing a vehicle interior.

BACKGROUND

Various locations, which may be contaminated by the body contact of a passenger, such as a steering handle, a door handle, and a console box exist in a vehicle interior, and frequent cleaning and sterilization and the like may be regarded as being required for hygienic use.

Particularly, in the case of a vehicle used for car sharing or the like, as described above, a location which the user's body frequently contacts may become a part of the transmission path capable of spreading infectious diseases between various passengers.

The information disclosed in the Background section above is to aid in the understanding of the background of the present disclosure, and should not be taken as acknowledgement that this information forms any part of prior art.

SUMMARY

An object of the present disclosure is to provide a sterilizer for a vehicle and a control method thereof, which may easily and locally sterilize a contamination site or a contamination possible site of a vehicle interior, thereby implementing the hygienic use of a vehicle, and furthermore, preventing the vehicle from becoming the transmission path of infectious diseases.

A sterilizer for a vehicle for achieving the object is configured to include: a module bracket fixed to an interior component of a vehicle; a slider slidably mounted on the module bracket; a module case connected to the slider; a sterilization module disposed within the module configured to radiate ultraviolet rays to an outside; and a motor fixed to the module bracket to drive the slider by a passenger's request.

The module bracket may be fixed to a back of a surface of the interior component, and the slider may be configured such that the module case penetrates the interior component and is movable upwardly to protrude from the surface of the interior component by driving the motor.

The module case may be rotatably connected to the slider, and a torsion spring may be arranged between the module case and the slider, and may be configured to elastically support the module case such that the module case is rotated at a predetermined angle with respect to the slider when the module case protrudes from the surface of the interior component.

The predetermined angle may be an angle at which the module case protrudes from the surface of the interior component to be rotated with respect to the slider, thereby sterilizably radiating ultraviolet rays to a sterilization-required site of the interior component.

The module case may be aligned in a direction in which the slider moves upward and downward when the module case 5 is inserted into the interior component.

The module case may be tilted with respect to the slider as the module case protrudes from the surface of the interior component, and a tilt angle of the module case with respect to the slider may become the predetermined angle when one end of the module case, rotatably connected to the slider, protrudes from the surface of the interior component.

The slider may include a driving groove into which a pinion of the motor is inserted, and one side of the driving groove may include a rack to which the pinion of the motor is engaged.

The driving groove may be opened such that one end of the slider opposing another end of the slider to which the module case is connected may be detachable from the pinion of the motor.

The sterilization module may be configured to include: an LED for emitting ultraviolet rays for sterilization; a body sensing sensor for sensing a presence or absence of a body of a passenger within a sterilizable region of the ultraviolet rays emitted by the LED; and a module controller for controlling driving of the LED according to a signal of the body sensing sensor.

The sterilization module may be configured to further include: a distance measurement sensor for measuring a distance between a location at which ultraviolet rays emitted by the sterilization module are radiated and the sterilization module; and a display device for displaying whether the distance is within a sterilization optimal distance by the module controller according to the distance information measured by the distance measurement sensor.

The sterilization module may have a communication device for receiving an operation input of the passenger and receiving state information of the vehicle by a communication with an interior controller installed on an interior of the vehicle, and the module controller may be configured to control the LED according to information received by the communication device.

The communication device may be configured to receive the operation input of the passenger by the communication with a portable wireless terminal of the passenger, and the module controller may be configured to control the LED according to the operation input of the passenger received from the portable wireless terminal and the state information of the vehicle received from the interior controller, which are received by the communication device.

Further, a method for controlling a sterilizer for a vehicle for achieving the object is configured to include: directing, by an interior controller of the vehicle, an LED of a sterilization module to a sterilization request site by moving a slider by driving a motor such that a module case protrudes from a surface of an interior component, when receiving a sterilization request operation input of a passenger; starting, by a module controller, sterilization by turning off the LED when a body of a passenger exists by sensing a presence or absence of the body in the sterilization request site, and turning on the LED only when the body does not exist, and continuing, by the module controller, the sterilization during a predetermined reference time, after the sterilization starts.

While continuing the sterilization during the reference time, when sensing that the body approaches the sterilization request site, the module controller may turn off the LED to terminate the sterilization operation.

The interior component on which the sterilizer for a vehicle is mounted is a door window switch module of a door, and in the case where a sterilization site of the sterilizer for a vehicle is a surface of the door window switch module, and when recognizing that the door on which the door window switch module is mounted is opened while continuing the sterilization, the module controller may turn off the LED to terminate the sterilization operation.

The present disclosure may be configured to include: moving, by the interior controller, the slider up to a predetermined reference height such that the module case protrudes to the surface of the interior component by driving the motor, when a portable request of the passenger is input; and facilitating detachment of the sterilizer by freely rotating the motor when the passenger intends to pull the sterilizer to be separated from the interior component, after the slider moves up to the reference height.

The present disclosure may easily and locally sterilize the contamination site or the contamination possible site of the vehicle interior, thereby implementing the hygienic use of the vehicle, and furthermore, preventing the vehicle from becoming the transmission path of infectious diseases.

BRIEF DESCRIPTION OF THE DRAWINGS

The above and other objects, features and other advantages of the present disclosure will be more clearly understood from the following detailed description when taken in conjunction with the accompanying drawings, in which:

FIG. 1 is an exploded perspective diagram illustrating a sterilizer for a vehicle according to an exemplary embodiment of the present disclosure.

FIG. 2 is a diagram illustrating a state where the sterilizer for a vehicle according to an exemplary embodiment of the present disclosure is mounted on a door window switch module of a vehicle.

FIG. 3 is a diagram illustrating a state where the sterilizer for a vehicle according to an exemplary embodiment of the present disclosure is viewed from the inside of the door window switch module illustrated in FIG. 2.

FIG. 4 is a diagram specifically illustrating a coupling structure of a slider and a motor of the sterilizer for a vehicle according to an exemplary embodiment of the present disclosure.

FIG. 5 is a diagram explaining an elastic rotation structure of the slider and a module case of the sterilizer for a vehicle according to an exemplary embodiment of the present disclosure.

FIG. 6 is a diagram illustrating a process in which the module case of the sterilizer for a vehicle according to an exemplary embodiment of the present disclosure protrudes to the surface of an interior component to be directed to a sterilization request site.

FIG. 7 is a diagram explaining a process in which the sterilizer for a vehicle according to an exemplary embodiment of the present disclosure is used for portable use by the portable request of a passenger.

FIG. 8 is a diagram conceptually illustrating an interior controller of a vehicle and a portable terminal of the user which interact with the sterilizer for a vehicle according to an exemplary embodiment of the present disclosure.

FIG. 9 is a flowchart illustrating an exemplary embodiment of a method for controlling the sterilizer for a vehicle according to an exemplary embodiment of the present disclosure.

DETAILED DESCRIPTION OF THE DISCLOSURE

Referring to FIGS. 1 to 8, a sterilizer for a vehicle according to some exemplary embodiments of the present disclosure is configured to include a module bracket 1 fixed to an interior component P of a vehicle, a slider 3 slidably mounted on the module bracket 1, a module case 5 connected to the slider 3, a sterilization module 7 configured to be provided within the module case 5 to radiate ultraviolet rays to the outside, and a motor 9 fixed to the module bracket 1 to drive the slider 3 by the passenger's request.

That is, the sterilizer for a vehicle according to the present disclosure is mounted on a vehicle in a state of being movable with respect to the interior component P of a vehicle by the motor 9 and the slider 3, and performs a sterilization function by radiating the ultraviolet rays to the outside of the module case 5 through the mounted sterilization module 7.

In the present exemplary embodiment, the module bracket 1 is fixed to the back of the surface of the interior component P, and the slider 3 is installed such that the module case 5 may penetrate and protrude to the outside of the surface of the interior component P by the driving of the motor 9.

That is, the slider 3 is formed with a driving groove 13 into which a pinion 11 of the motor 9 is inserted, and one side of the driving groove 13 is formed with a rack 15 to which the pinion 11 of the motor 9 is engaged, such that when the motor 9 is driven, the slider 3 performs the linear movement by operations of the pinion 11 and rack 15.

Here, the driving groove 13 has a structure in which the slider 3 is opened such that one end of the slider 3 opposing another end of the slider 3 to which the module case 5 is connected may be detachable from the pinion 11 of the motor 9.

Therefore, as described later, the structure in which the bottom of the driving groove 13 of the slider 3 is opened is configured such that upon the portable request of the passenger, as illustrated in FIG. 7, when the user pulls the module case 5, the slider 3 may be completely separated from the motor 9 and the interior component P to use the sterilizer for portable use, and after the use is completely terminated, the pinion 11 of the motor 9 may be inserted into the driving groove 13 of the slider 3 again.

In the present exemplary embodiment, the interior component P is a door window switch module 17, and as illustrated, the module bracket 1 is fixed to the bottom of the door window switch module 17, and the motor 9 is fixed to the module bracket 1, such that when the pinion 11 of the motor 9 is rotated, the slider 3 penetrates the door window switch module 17 to move upward and downward, and therefore, the module case 5 connected to the top of the slider 3 also penetrates the door window switch module 17 together to move upward and downward.

The present exemplary embodiment uses the door window switch module 17 as the interior component P but additionally, as a component mounted on the vehicle interior, all components which are likely to be contaminated by the passenger's hand or the like may correspond to the interior component P, such that for example, a console, an overhead console, a seatbelt fastening part, a steering wheel, and the like are included in the interior component P on which the sterilizer according to the present disclosure may be mounted.

The module case 5 is connected to be rotatable at a predetermined angle with respect to the slider 3, and when the module case 5 protrudes to the outside of the interior component P, a torsion spring 19 for elastically supporting the module case 5 to be rotatable at a predetermined angle with respect to the slider 3 is provided between the module case 5 and the slider 3.

The predetermined angle is an angle at which the module case 5 protrudes to the outside of the interior component P to be rotated with respect to the slider 3 while minimizing the size of a hole through which the slider 3 and the module case 5 penetrate the interior component P to slide, thereby sterilizably radiating ultraviolet rays to a sterilization-required site of the interior component P.

That is, referring to FIG. 6, in a state where the slider 3 and the module case 5 have maximally moved downward, the top surface of the module case 5 forms the surface of the same height as the top surface of the door window switch module 17 which is the interior component P, thereby securing a beautiful appearance, and when the slider 3 moves upward for the sterilization function, the module case 5 is automatically tilted toward the sterilization-required site by the torsion spring 19.

Therefore, the predetermined angle is set to an angle at which the module case 5 is required to be tilted with respect to the slider 3 in order to sterilize all of switches which are likely to be contaminated by the passenger's contact at an appropriate level, in consideration of the rising height of the module case 5, a sterilizable range of ultraviolet rays by an LED of the sterilization module 7 mounted within the module case 5, and the like, and may be appropriately set by multiple experiments and analyses.

Here, minimizing the size of the hole 21 through which the slider 3 and the module case 5 penetrate the interior component P to slide is to form the hole 21 such that a large gap is not possibly formed between the door window switch module 17 and the module case 5, when the module case 5 is inserted into the interior component P in the state of being aligned in the direction in which the slider 3 moves upward and downward, rather than a state where the module case 5 is tilted with respect to the slider 3 when the slider 3 and the module case 5 are inserted into the interior component P, and thus the top surface of the module case 5 becomes the same surface as the top surface of the door window switch module 17 as described above.

That is, when moving upward through the hole 21 of the door window switch module 17, the module case 5 moves upward in the state of being aligned in the same direction as the direction in which the slider 3 moves upward, thereby minimizing the hole 21 of the door window switch module 17 compared to the case where the module case 5 penetrates the hole 21 in the state of being tilted with respect to the slider 3.

As detailed above, the module case 5 is tilted with respect to the slider 3 as the module case 5 protrudes from the surface of the interior component P and a tilt angle of the module case 5 with respect to the slider 3 becomes the predetermined angle when one end of the module case 5, rotatably connected to the slider 3, protrudes from the surface of the interior component P.

For reference, FIG. 1 illustrates a hinge shaft 41 acting as a rotary shaft of the module case 5 with respect to the slider 3, and a cover 43 for closing the module case 5 after the sterilization module 7 is inserted into the module case 5 together.

Referring to FIG. 8, the sterilization module 7 is configured to include a light-emitting diode (LED) 23 for emitting ultraviolet rays for sterilization, a body sensing sensor 25 for sensing the presence or absence of the body within a sterilizable region of the ultraviolet rays emitted by the LED 23, and a module controller 27 for controlling the driving of the LED 23 according to a signal of the body sensing sensor 25.

That is, the LED 23, the body sensing sensor 25, the module controller 27, and the like are provided on an electronic circuit board to configure the sterilization module 7.

The module controller 27 of the sterilization module 7 according to an exemplary embodiment of the present disclosure may be a processor (e.g., computer, microprocessor, CPU, ASIC, circuitry, logic circuits, etc.). The module controller 27 may be implemented by a non-transitory memory storing, e.g., a program(s), software instructions reproducing algorithms, etc., which, when executed, controls operations of various components of the sterilization module 7, and a processor configured to execute the program(s), software instructions reproducing algorithms, etc.

According to an exemplary embodiment, the module case 5 may have a transparent window so as to radiate the ultraviolet rays generated by the embedded LED 23 of the sterilization module 7 to the outside, or have a configuration in which the LED 23 may protrude to the surface of the module case 5.

As the body sensing sensor 25, an electrostatic sensor in which an electrostatic capacity is changed when the passenger's body approaches, an ultrasonic sensor, an infrared sensor, or the like may be used.

As the LED 23, an LED emitting ultraviolet-C (UV-C) rays with proven sterilization performance may be used.

Therefore, the module controller 27 determines whether the body exists within the sterilizable region in which ultraviolet rays are radiated and thus sterilization is to be performed before driving the LED 23; when the existence of the body is sensed, the module controller 27 does not drive the LED 23 and terminates the requested sterilization operation to be prepared for safety accidents; and when the approach of the body within the sterilizable region is sensed by the body sensing sensor 25 and it is determined that there is a dangerous situation even in the middle of performing the sterilization, the module controller 27 may turn off the LED 23 and terminate the sterilization operation.

Further, the sterilization module 7 may be configured to further include a distance measurement sensor 29 for measuring a distance between a location at which the ultraviolet rays emitted by the sterilization module 7 are radiated and the sterilization module 7, and a display device 31 provided to display whether the distance is within a sterilization optimal distance by the module controller 27 according to the distance information measured by the distance measurement sensor 29.

This is to prepare for a case where the passenger makes the portable request, such that the sterilizer is completely separated from the interior component P such as the door window switch module 17 to be used for portable use, and to measure the distance between an object to be sterilized and the sterilizer according to the present disclosure by the distance measurement sensor 29 to display the case where the distance is within the sterilization optimal distance at which the sterilization may be well performed and the case where the distance is not within the sterilization optimal distance on the display device 31, thereby allowing the passenger to use the sterilizer according to the present disclosure easily and effectively.

Therefore, the distance measurement sensor 29 may be implemented by various sensors from the ultrasonic sensor capable of short-range measurement or the like to a laser sensor or the like; the display device 31 may be implemented by various devices such as an LED or a color lamp which may distinguish the case where the distance is within the sterilization optimal distance at which the sterilization may be well performed and the case where the distance is not within the sterilization optimal distance with a color; and of course, the display device 31 is required to be installed to display the display contents on the surface of the module case 5.

Further, the sterilization module 7 has a communication device 35 which may receive an operation input of the passenger and receive state information of a vehicle by the communication with the interior controller 33 installed on the vehicle interior, and the module controller 27 is configured to control the LED 23 according to the information received by the communication device 35.

The interior controller 33 may be configured to be connected to a user interface 37 provided in the vehicle interior to receive the user's intention requiring the operation of the sterilizer, thus to communicate with the communication device 35 of the module controller 27, and to drive the motor 9 of the sterilizer for a vehicle.

The communication device 35 may be implemented with various electronic circuits to perform various functions, for example, noise filtering, A/D conversion, encoding/decoding and modulating. The communication device 35 may be a hardware device implemented by various electronic circuits to transmit and receive signals via wireless or wired connections.

The interior controller 33 and the user interface 37 may also be implemented in the conventional vehicle interior device such as a conventional navigation or an audio, video, navigation (AVN) together, and may also add a separate device.

Therefore, when the passenger inputs the use intention of the sterilizer in the method illustrated in FIG. 6 using the user interface 37, the interior controller 33 controls the motor 9 such that the slider 3 and the module case 5 move upward, and when it is determined that the module case 5 has been directed to the sterilization request site by the rising of the slider 4 through the communication device 35, the module controller 27 drives the LED 23 such that the sterilization request site of the interior component P is sterilized.

Meanwhile, the communication device 35 may be configured to include the function capable of receiving the operation input of the passenger by the communication with a portable wireless terminal 39 of the passenger.

In this case, the module controller 27 may be configured to control the LED 23 according to the operation input of the passenger from the portable wireless terminal 39 and the vehicle state information from the interior controller 33, which are received by the communication device 35.

Therefore, the passenger may request the operation of the sterilizer through the portable wireless terminal 39 such as a smartphone owned by the passenger as well as the user interface 37 mounted on the vehicle.

Further, the vehicle state information received from the interior controller 33 may become, for example, information about the opening or closing of a door or the like, such that as described later, the module controller 27 may stop the driving of the LED 23 to terminate the sterilization operation if the door is opened while performing the sterilization operation.

FIG. 9 is a flowchart illustrating a method for controlling the sterilizer for a vehicle according to an exemplary embodiment of the present disclosure, and the method is configured to include directing, by the interior controller 33, the LED 23 of the sterilization module 7 to the sterilization request site by moving the slider 3 by the driving of the motor 9 and protruding the module case 5 to the surface of the interior component P when receiving the sterilization request operation of the passenger (S10); starting, by a module controller 27, sterilization by turning off the LED 23 if the presence or absence of the body is sensed in the sterilization request site and the body exists, and turning on the LED 23 only if the body does not exist (S20); and continuing, by the module controller 27, the sterilization during a predetermined reference time after the sterilization starts (S30).

Here, the sterilization request operation of the passenger is the sterilization request for the interior component on which the sterilizer is mounted, and this is distinguished from the portable request to be described later.

That is, the portable request allows the passenger to completely detach and separate the sterilizer from the interior component P on which the sterilizer is mounted and to protrude the sterilizer from the interior component P for sterilization elsewhere desired by the passenger, and the sterilization request operation is a request for sterilizing the sterilization-required site of the device on which the sterilizer is installed.

Further, the sterilization request site is a site to be sterilized by the passenger performing the sterilization request operation as described above, and substantially means a predetermined sterilization site of the interior component P on which the sterilizer is mounted, such that as illustrated in FIG. 6, if the interior component P is the door window switch module 17, a plurality of switch operation parts of the door window switch module 17 become the sterilization request site.

Of course, the sterilization request site varies depending on the interior component P on which the sterilizer is mounted.

The module controller 27 determines whether the body is located at a site in which the sterilization is performed by the body sensing sensor 25 and starts the sterilization by turning on the LED 23 only if the body does not exist, and continues the sterilization during the reference time.

The reference time is preferably set to an appropriate time at which the sterilization at the corresponding sterilization site may be completed by the radiation of the ultraviolet rays of the LED 23.

While continuing the sterilization during the reference time, when sensing that the body approaches the sterilization request site, the module controller 27 terminates the sterilization operation by turning off the LED 23, thereby preventing the occurrence of the safety accidents.

Meanwhile, the interior component P on which the sterilizer for a vehicle is mounted is the door window switch module 17 of the door, and in the case where the sterilization site of the sterilizer for a vehicle is the surface of the door window switch module 17, when recognizing that the door on which the door window switch module 17 is mounted is opened while continuing the sterilization, the module controller 27 terminates the sterilization operation by turning off the LED 23, thereby avoiding possible dangerous situation.

Here, the module controller 27 receives information about whether the door is opened from the interior controller 33 through the communication device 35 to control the LED 23.

Meanwhile, the control method according to the present disclosure includes moving, by the interior controller 33, the slider 3 up to a predetermined reference height such that the module case 5 protrudes to the surface of the interior component P by driving the motor 9, when the portable request of the passenger is input (S110), and facilitating the detachment of the sterilizer by freely rotating the motor 9 when the passenger intends to pull the sterilizer to be separated from the interior component P, after the slider 3 moves up to the reference height (S120).

The reference height is appropriately set to move the module case 5 upward at the level suitable for pulling such that the passenger separates the sterilizer from the interior component P as described above.

Therefore, the passenger may hold the module case 5 located at the top of the slider 3 moving upward up to the reference height or the slider 3 to separate the sterilizer from the interior component P, thereby freely sterilizing the place desired by the passenger, and returning the sterilizer to the interior component P again.

While the specific exemplary embodiment of the present disclosure has been illustrated and described, it will be apparent to those skilled in the art that the present disclosure may be variously improved and changed without departing from the technical spirit of the present disclosure provided by the appended claims.

What is claimed is:

1. A sterilizer for a vehicle comprising:
   a module bracket fixed to an interior component of a vehicle;
   a slider slidably mounted on the module bracket;
   a module case connected to the slider;
   a sterilization module disposed within the module case and configured to radiate ultraviolet rays to an outside;
   a motor fixed to the module bracket to drive the slider by a passenger's request; and
   an interior controller configured to move the slider up to a predetermined reference height such that the module case protrudes to a surface of the interior component by driving the motor when a portable request of the passenger is input, and to facilitate detachment of the sterilizer by freely rotating the motor when the passenger pulls the sterilizer to be separated from the interior component, after the slider moves up to the predetermined reference height.

2. The sterilizer for a vehicle according to claim 1,
   wherein the module bracket is fixed to a back of the surface of the interior component, and
   wherein the slider is configured such that the module case penetrates the interior component and is movable upwardly to protrude from the surface of the interior component by driving the motor.

3. The sterilizer for a vehicle according to claim 1,
   wherein the module case is rotatably connected to the slider, and
   wherein a torsion spring is arranged between the module case and the slider, and is configured to elastically support the module case such that the module case is rotated at a predetermined angle with respect to the slider when the module case protrudes from the surface of the interior component.

4. The sterilizer for a vehicle according to claim 3,
   wherein the predetermined angle is an angle at which the module case protrudes from the surface of the interior component to be rotated with respect to the slider, thereby sterilizably radiating ultraviolet rays to a sterilization-required site of the interior component.

5. The sterilizer for a vehicle according to claim 4,
   wherein the module case is aligned in a direction in which the slider moves upward and downward when the module case 5 is inserted into the interior component.

6. The sterilizer for a vehicle according to claim 5,
   wherein the module case is tilted with respect to the slider as the module case protrudes from the surface of the interior component, and a tilt angle of the module case with respect to the slider becomes the predetermined angle when one end of the module case, rotatably connected to the slider, protrudes from the surface of the interior component.

7. The sterilizer for a vehicle according to claim 1,
   wherein the slider includes a driving groove into which a pinion of the motor is inserted, and
   wherein one side of the driving groove includes a rack to which the pinion of the motor is engaged.

8. The sterilizer for a vehicle according to claim 7,
   wherein the driving groove is opened such that one end of the slider opposing another end of the slider to which the module case is connected is detachable from the pinion of the motor.

9. The sterilizer for a vehicle according to claim 1,
   wherein the sterilization module comprises:
   an LED for emitting ultraviolet rays for sterilization;
   a body sensing sensor for sensing a presence or absence of a body of a passenger within a sterilizable region of the ultraviolet rays emitted by the LED; and
   a module controller for controlling driving of the LED according to a signal of the body sensing sensor.

10. The sterilizer for a vehicle according to claim 9,
    wherein the sterilization module further comprises:
    a distance measurement sensor for measuring a distance between a location at which ultraviolet rays emitted by the sterilization module are radiated and the sterilization module; and
    a display device for displaying whether the distance is within a sterilization optimal distance by the module controller according to the distance information measured by the distance measurement sensor.

11. The sterilizer for a vehicle according to claim 9,
    wherein the sterilization module has a communication device for receiving an operation input of the passenger and receiving state information of the vehicle by a communication with the interior controller installed on an interior of the vehicle, and
    wherein the module controller is configured to control the LED according to information received by the communication device.

12. The sterilizer for a vehicle according to claim 11,
    wherein the communication device is configured to receive the operation input of the passenger by the communication with a portable wireless terminal of the passenger, and
    wherein the module controller is configured to control the LED according to the operation input of the passenger received from the portable wireless terminal and the state information of the vehicle received from the interior controller, which are received by the communication device.

13. A method for controlling a sterilizer for a vehicle, the method comprising:
    directing, by an interior controller of the vehicle, an LED of a sterilization module to a sterilization request site by moving a slider by driving a motor such that a module case protrudes from a surface of an interior component, when receiving a sterilization request operation input of a passenger;
    starting, by a module controller, sterilization by turning off the LED when a body of a passenger exists by sensing a presence or absence of the body in the sterilization request site, and turning on the LED only when the body does not exist;

continuing, by the module controller, the sterilization during a predetermined reference time, after the sterilization starts;

moving, by the interior controller, the slider up to a predetermined reference height such that the module case protrudes to the surface of the interior component by driving the motor, when a portable request of the passenger is input; and facilitating detachment of the sterilizer by freely rotating the motor when the passenger pulls the sterilizer to be separated from the interior component, after the slider moves up to the predetermined reference height.

14. The method according to claim 13, wherein while continuing the sterilization during the reference time, when sensing that the body approaches the sterilization request site, the module controller turns off the LED to terminate the sterilization operation.

15. The method according to claim 13, wherein the interior component on which the sterilizer for a vehicle is mounted is a door window switch module of a door, and in the case where a sterilization site of the sterilizer for a vehicle is a surface of the door window switch module, and when recognizing that the door on which the door window switch module is mounted is opened while continuing the sterilization, the module controller turns off the LED to terminate the sterilization operation.

* * * * *

UNITED STATES PATENT AND TRADEMARK OFFICE
CERTIFICATE OF CORRECTION

| | |
|---|---|
| PATENT NO. | : 11,771,783 B2 |
| APPLICATION NO. | : 17/154001 |
| DATED | : October 3, 2023 |
| INVENTOR(S) | : Jae Seung Lee and Young Hoon Ji |

It is certified that error appears in the above-identified patent and that said Letters Patent is hereby corrected as shown below:

On the Title Page

Column 1, Item (73), replace the present listing with the following:
-- (73) Hyundai Motor Company, Seoul (KR); KIA Motors Corporation, Seoul (KR); KAIS Inc., Pyeongtaek-si (KR) --

Signed and Sealed this
Twenty-first Day of November, 2023

*Katherine Kelly Vidal*

Katherine Kelly Vidal
*Director of the United States Patent and Trademark Office*